United States Patent [19]

Green et al.

[11] 3,934,144
[45] Jan. 20, 1976

[54] X-RAY MACHINE FOR RAPID AND PRECISE INSPECTION OF MIXED SIZES OF PNEUMATIC TIRES

[75] Inventors: Donald T. Green, Mentor; James L. Snarr, Eastlake, both of Ohio

[73] Assignee: United States Steel Corporation, Pittsburgh, Pa.

[22] Filed: Apr. 11, 1974

[21] Appl. No.: 459,895

[52] U.S. Cl. ............................................. 250/358 T
[51] Int. Cl.² ......................................... G01N 23/00
[58] Field of Search ...................... 250/360, 358 T

[56] References Cited
UNITED STATES PATENTS

| | | | |
|---|---|---|---|
| 3,550,443 | 12/1970 | Sherkin | 250/360 |
| 3,789,226 | 1/1974 | Green et al. | 250/360 |

*Primary Examiner*—Davis L. Willis
*Attorney, Agent, or Firm*—Harold S. Meyer

[57] ABSTRACT

An X-ray tire inspection machine for rapid and precise determination of accuracy of placement of internal elements, by visual or automated sensing of dimensions and of uniformity, precisely places each of a random succession of pneumatic tires for highway vehicles from the smallest to the largest sizes, scans the entirety of bead-to-bead sectors or any part of each sector, without gaps or significant overlaps, and displays all or any desired portions of the X-ray shadow pictures as a succession of still pictures, or senses automatically the presence of irregularities of various kinds in any desired locations. Precise placement of tires is accomplished by gripping of the tread of a horizontal tire by four spools having upper and lower flanges positively moved toward one another at a fixed speed until they grip the shoulders of the tread. Precise location of internal elements is accomplished by simultaneous introduction into the bead circle, exactly midway between the upper and lower supporting flanges, of a bead spreading device and an X-ray source directed toward the tire.

16 Claims, 23 Drawing Figures

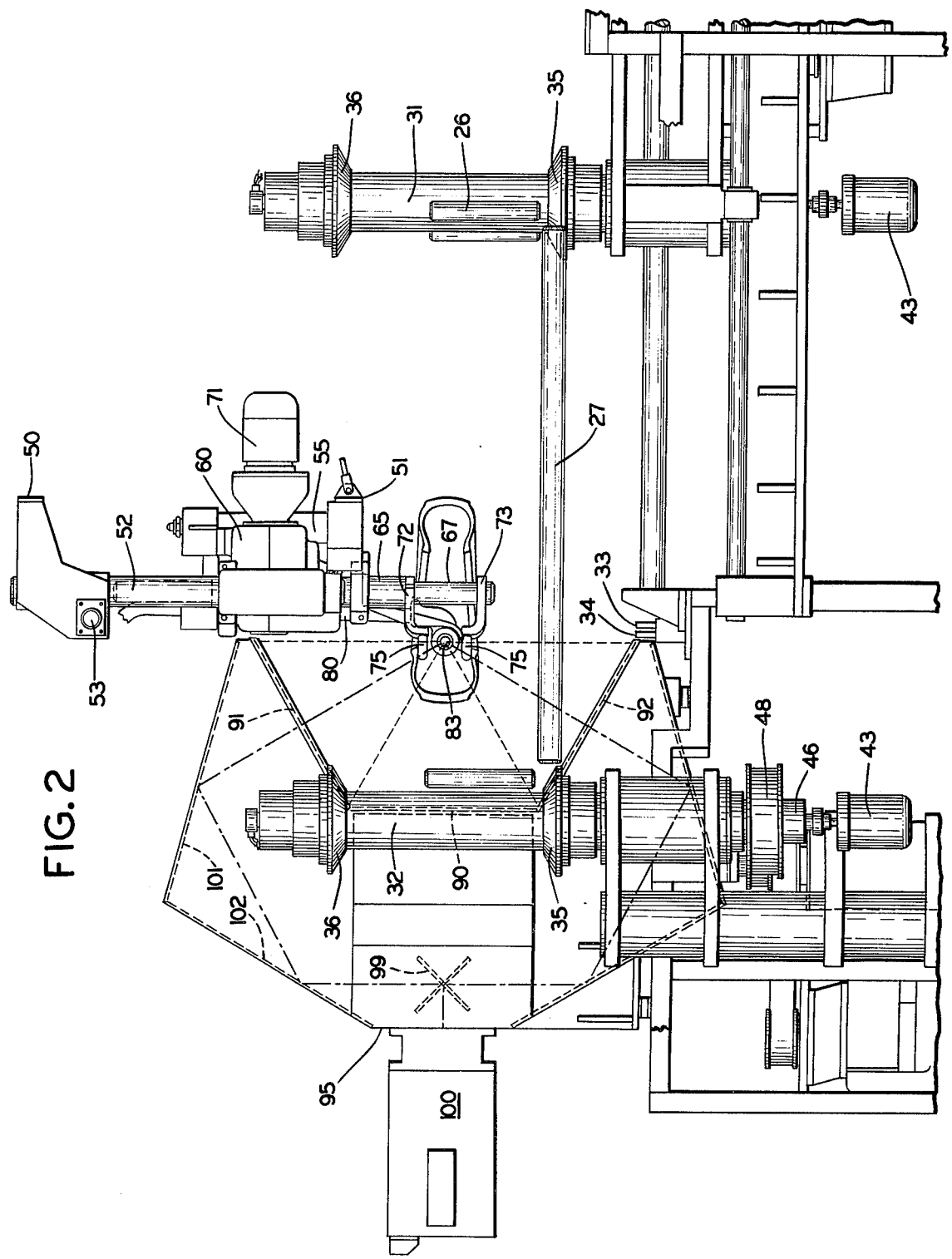

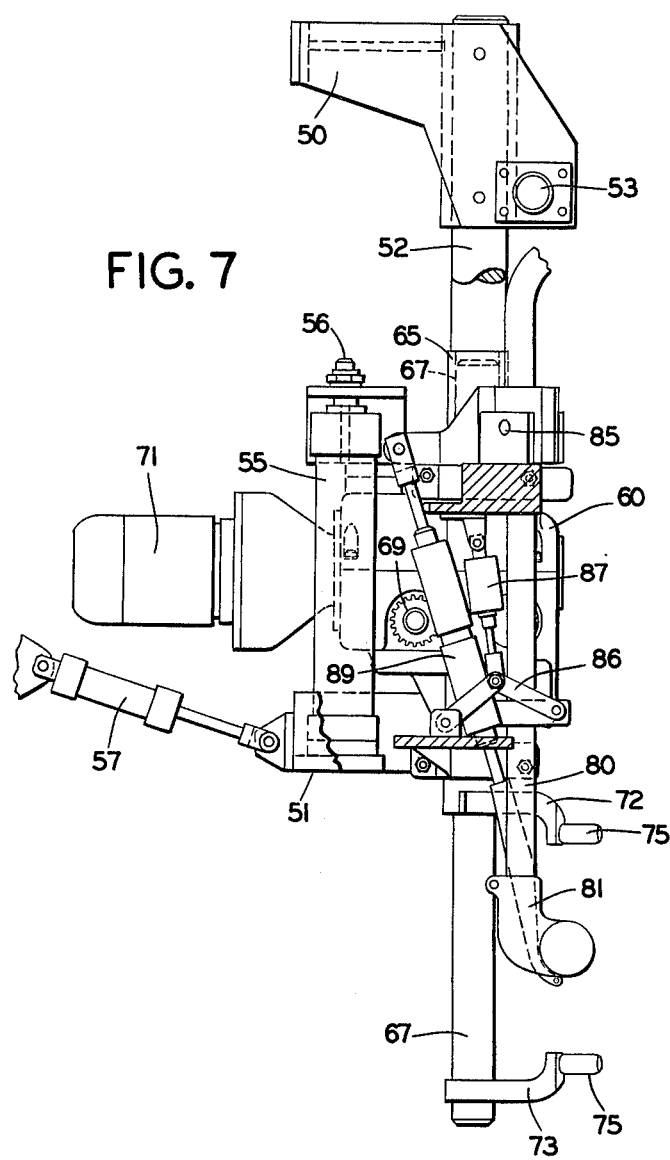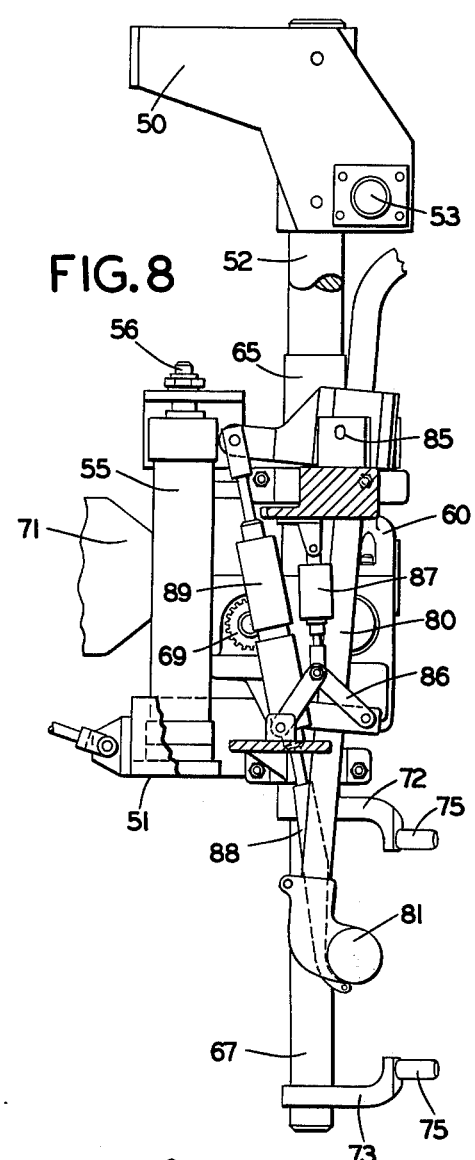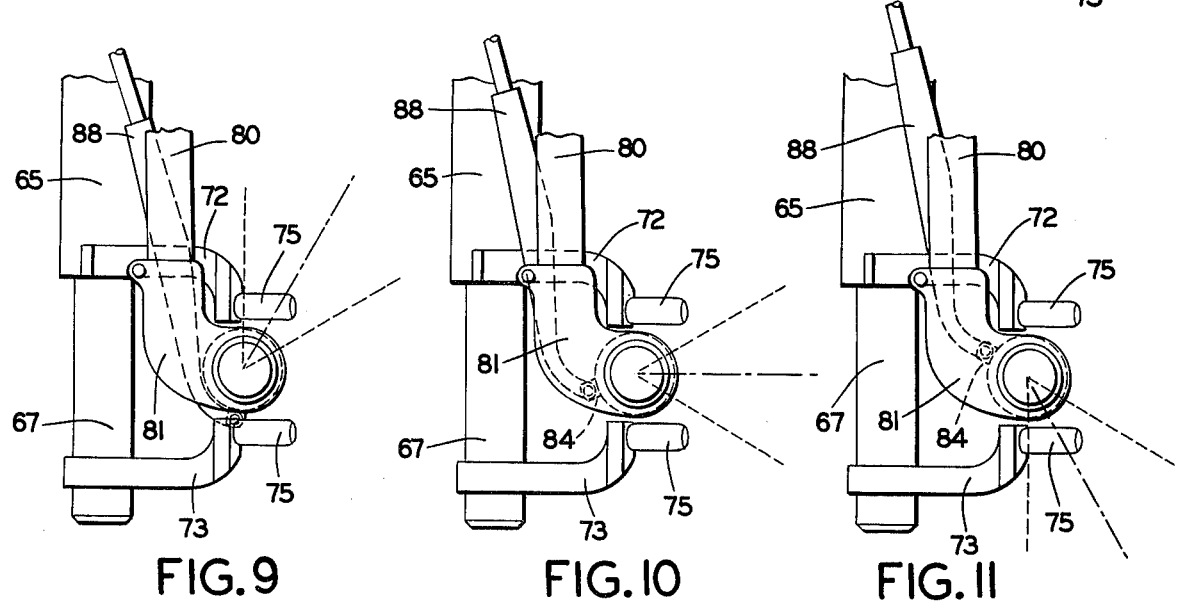

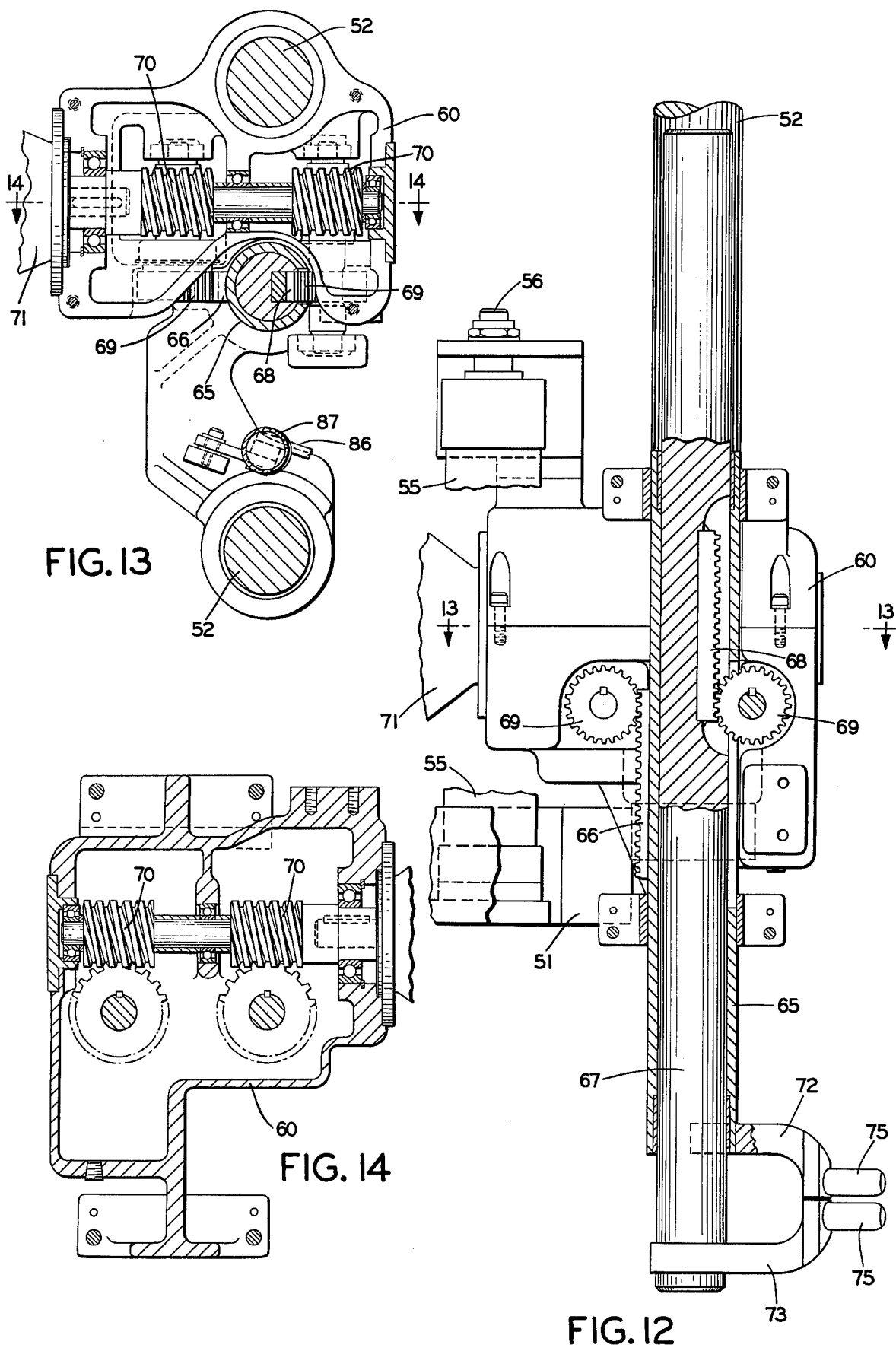

X-RAY MACHINE FOR RAPID AND PRECISE INSPECTION OF MIXED SIZES OF PNEUMATIC TIRES

CROSS-REFERENCES

This invention may include the stepwise scanning, with display of a succession of still pictures, of the patent of Green and Snarr U.S. Pat. No. 3,758,723 dated Sept. 11, 1973; the automatic tire handling devices of the patent of Green and Snarr U.S. Pat. No. 3,789,226 dated Jan. 29, 1974; and the optical system for depicting in a single picture the internal structure of a bead-to-bead sector of a tire, of the application for patent of Green and DeBenedetti Ser. No. 455,544 filed Mar. 28, 1974; all owned by the owner of this invention.

BACKGROUND

Pneumatic tires for highway service are subjected to severe stresses from the heavy loads, high driving and braking torque, cornering forces, and high speed flexing, which occur in present day operation. Even the most modern tire building equipment does not always place the internal elements with the intended degree of uniformity, and the final molding operation hides non-uniform placement which can lead to stress concentration and consequent premature failure, so that external inspection is not adequate for separating good tires from bad ones.

The most successful procedure for locating defects in internal placement of elements of pneumatic tires is X-ray inspection, but in spite of many recent advances, it has continued to be so slow and expensive that routine inspection of every tire has added significantly to cost and therefore to sales price.

An object of this invention accordingly is to automate the operation of an X-ray inspection machine, so that it will require a minimum of attention and therefore a minimum labor cost.

Another object is to make an X-ray inspection machine of maximum versatility so that it can handle random mixes of types and sizes as they appear in production operations without requiring any expensive pre-sorting. Still another object is to provide equipment which will accept the smallest highway tires in spite of the difficult geometrical problems of fitting into a small bead circle an X-ray tube of irreducible size because of the need for very high voltage insulation, and bead spreading mechanism of adequate size and strength so that it will also separate the large and stiff beads of large highway truck tires.

A further object is to provide a machine which can be used optionally for 100% visual inspection or for automated examination for specific conditions, or for both together or sequentially.

SUMMARY OF THE INVENTION

In this invention, in its preferred form, a continuous succession of tires which may be a random sequence of tires of widely varying sizes and types, ranging from tires for miniature motor cars or light trailers, with bead diameters of 10 inches (25.4 cm.), to the largest and heaviest highway truck tires, with bead diameters of 24.5 in. (62.1 cm.) or more, flow in a horizontal position on a roller conveyor to the X-ray inspection machine, where they are admitted one by one as the previous tire is discharged. The conveyor rollers at the entrance are skewed to direct the tires along a lateral fence, where a tire sensing device is located just beyond the center of the machine. Sensing of the presence of the advancing tire stops the conveyor and leaves the tire centered in the machine. It also triggers horizontal advance of a pair of spools with vertical axes, which engage the tread of the tire and push it laterally of the conveyor toward an X-ray imaging system. An electric eye has its vertical beam first interrupted and then exposed again as the open center of the tire passes opposite the electric eye. The passage of the light beam through the center of the tire stops advance of the spools, leaving the tire with the laterally most advanced part of the bead opening in a predetermined position. The light beam also triggers advance of another pair of spools with vertical axes, from the other side, toward the tire tread.

When the second pair of spools engage the tread of the tire with sufficient force to move the tire bead back into the beam of the electric eye, the advance of the spools is stopped and the upper and lower flanges of all of the spools are moved axially toward one another, one up and one down at the same speed along the cylindrical surfaces of the spools. The lower flanges, being initially closer to the tires, first engage the lower shoulder of the tire tread and lift the tire off the conveyor. When the upper flanges engage the opposite shoulder of the tire with a predetermined force, motion of the flanges is stopped, leaving the tire held with its midplane exactly at a predetermined level.

The stoppage of vertical motion of the flanges triggers vertical motion of a bead spreader mechanism and an X-ray tube head from a position above or below the tire to a position within the open center or bead circle of the tire. These elements are preferably mounted on a common support above the tire for simultaneous vertical downward movement. When they are centered with respect to the predetermined level of the midplane of the tire, they are moved horizontally to place the bead spreader fingers between the tire beads.

The bead spreader is preferably of the general type shown in the aforementioned U.S. Pat. No. 3,789,226, having two pairs of fingers, freely rotatable on their individual longitudinal axes, one pair for engaging one bead and the other pair for engaging the other bead, with their axes of rotation approximately radial to the tire. When the two pairs of fingers are separated vertically, they spread the beads in the sector where fingers are located without spreading the beads at the opposite part of the tire circumference, but permit easy rotation of the tire for complete examination of the entire circumference.

Because of the limited space in the bead circle of small highway tires, it is difficult to fit bead spreaders of adequate strength and also a suitable X-ray tube simultaneously into this space. The compact juxtaposition of these elements is accomplished in this invention by mounting each pair of bead spreader fingers on a bent plate, with a vertical face which carries the stub axles on which the fingers individually rotate, and a horizontal face which is connected to the end of a vertical support, with the X-ray tube in the space provided by the angles of the bent plates. The vertical supports are a pair of telescoping tubes which collectively make up a post for the bead spreaders and which are provided with a power drive for moving them at equal speed in opposite vertical directions.

The X-ray tube is preferably of the type which can be rotated on its longitudinal axis by suitable power mechanism, for directing the X-ray beam at different intervals of the inspection procedure toward different zones such as a bead and sidewall zone, the tread and shoulder zone, and the opposite bead and sidewall zone. For this purpose, the axis of rotation of the X-ray tube is placed in the midplane of the tire, and the focal spot from which the X-rays radiate is preferably placed close to the beads but not actually between them. Because of the length of the X-ray tube required for accommodating the high voltage elements and for accelerating and focusing the electron beam, the end most distant from the focal spot is thrust between the beads, and the hollow post which supports the tube and carries the electric cables is offset at the end which is connected to the tube so as to clear the beads when the tube is in operating position.

As already stated, the X-ray tube preferably is initially in the angle of the bead spreader supports, but is located closer to the tire beads during operation, for the most advantageous relation to the imaging system. This relocation of the X-ray tube is accomplished by pivoting the X-ray tube support on the bead spreader support, to move into the space provided by the spreading of the beads by separation of the bead spreader fingers. In the case of an X-ray tube having its focal spot near one end, the pivot is at a small angle to the pivot of the common support so as to move the focal spot from an off-center to an accurately centered position.

The X-ray tube is then swiveled into three successive positions, for directing X-rays through the three zones of the tire already mentioned, toward three adjacent fluorescent screens at an angle of about 120° to one another. These three screens form part of an imaging system of the type shown in the aforementioned application for patent. In this system, electronic images of the three shadow pictures on the screens are successively transmitted to adjacent thirds of the target of a storage tube to form a composite image of the entire width of the tire from bead to bead. The composite image is then displayed as a still picture on a picture tube of a monitor while the spools are rotated by a predetermined angle to bring another sector of the tire into position for similar imaging and display.

Alternatively, or additionally, photocells may be provided at critical locations, either for direct measurement of X-ray transmission, or for measurement of the light after transformation of the X-ray energy into light energy, for automatic sensing of the presence or absence of structural elements or of the proper spacing or density of structural elements.

THE DRAWINGS

In the accompanying drawings:

FIG. 2 is a transverse vertical section through the machine.

FIG. 7 is a partial section along the broken plane 7—7 of FIG. 5, with the bead spreaders and X-ray tube in operating position as they would be for the largest size highway tire.

FIG. 8 is a partial section similar of FIG. 7 but with the X-ray tube in its laterally retracted position.

FIG. 9 is a view similar to the lower part of FIG. 7 except that it shows the bead spreaders in position for the smallest highway tire, with the X-ray tube turned for scanning the upper bead and sidewall of the tire.

FIG. 10 is a view similar to FIG. 9 with the X-ray tube turned for scanning the tread or crown of the tire.

FIG. 11 is a view similar to FIGS. 9 and 10 with the X-ray tube turned for scanning the lower bead and sidewall of the tire.

FIG. 12 is a vertical section on a larger scale along the plane 12—12 of FIG. 5, showing the bead spreader driving racks.

FIG. 13 is a horizontal section along the plane 13—13 of FIG. 12 showing the gearing for the racks.

FIG. 14 is a vertical section along the plane 14—14 of FIG. 13.

Figure 21:
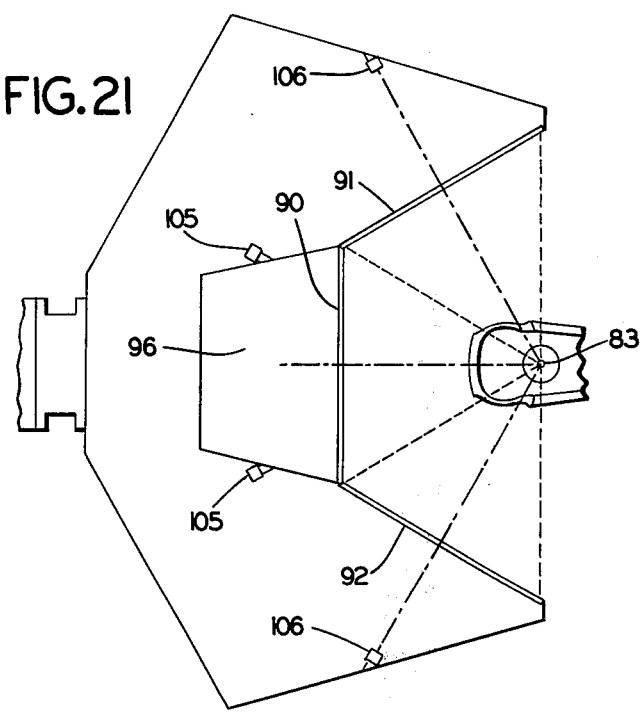
FIG. 21 is a diagrammatic elevation showing location of photocells for control of intensity of radiation.
Figure 22:
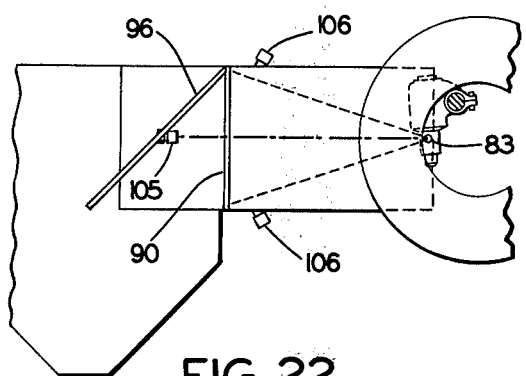

FIG. 22 corresponds to FIG. 21 in plan view.

Figure 23:
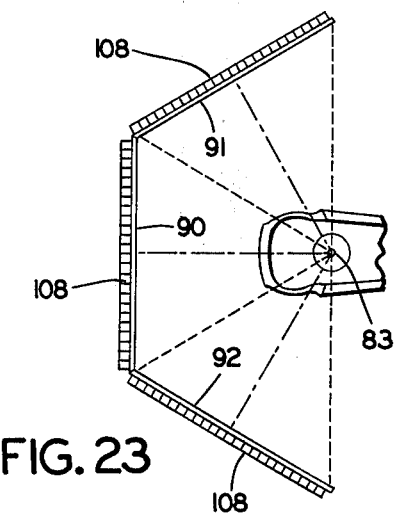

FIG. 23 is a diagrammatic view showing sensing devices for completely automatic inspection.

DETAILED DESCRIPTION

Figure 1:
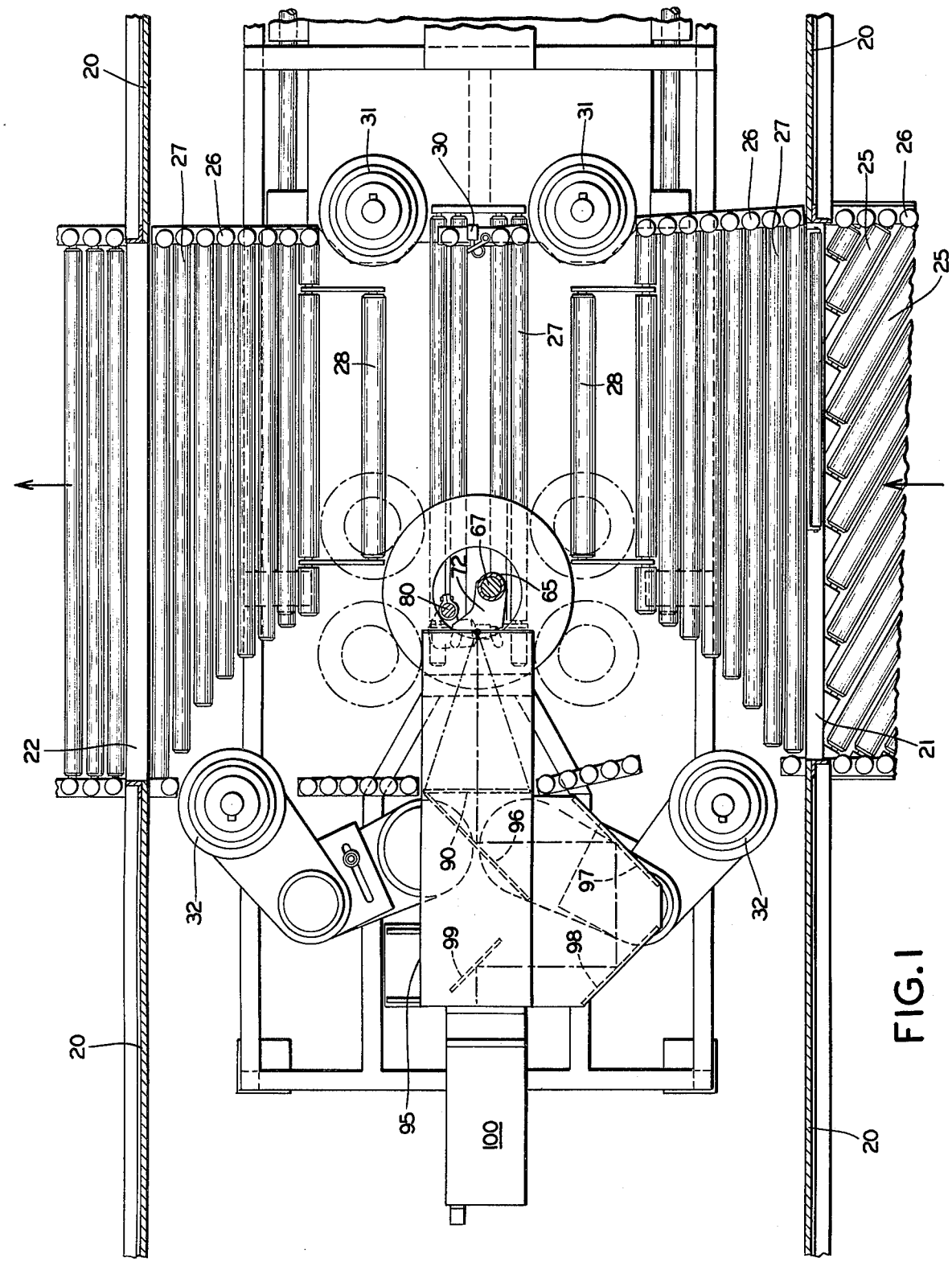
FIG. 1 is a plan view of the machine of this invention containing the smallest size tire which it will handle.
Figure 4:
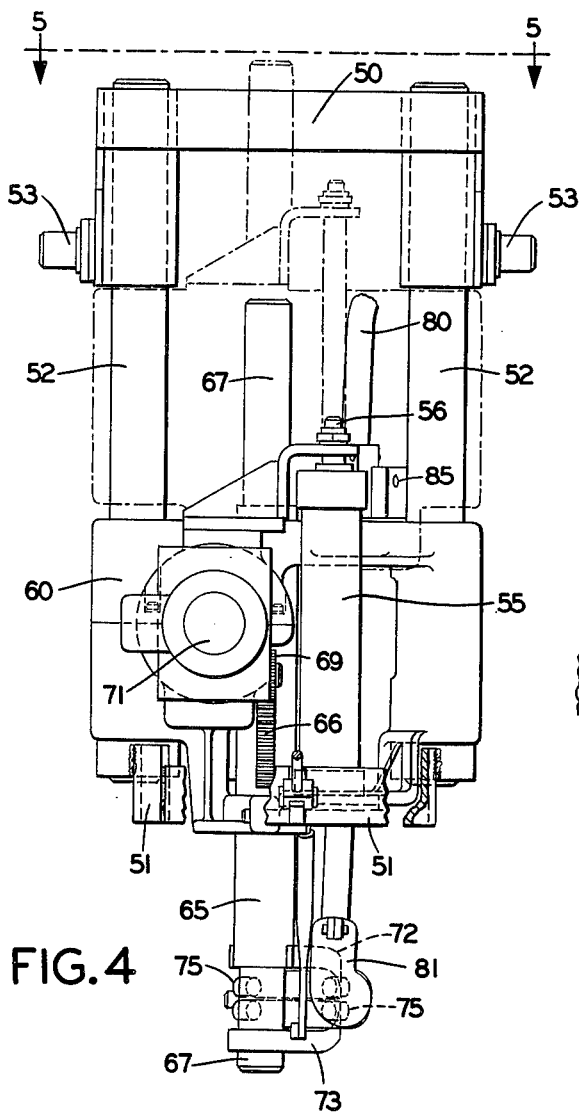
FIG. 4 is a view from the plane 4—4 of FIG. 3.

The tire inspection machine in the presently preferred form shown in FIGS. 1 and 2 is located in the path of a roller conveyor and is enclosed in the usual X-ray opaque lead shield 20 having a power operated inlet door 21, and an exit closure 22 which may be a flap of lead-loaded flexible material.

The portion of the conveyor system just in advance of the inlet 21 is composed of an array of skewed rollers 25 which guide each tire as it approaches the machine against a fence consisting of vertical rollers 26 so that each tire will enter the machine at one lateral extremity of the conveyor. The inlet door 21 is constructed to admit only one tire at a time, as is usual, and to admit the next tire only as the preceding one is on its way out of the exit.

The portion of the conveyor system within the machine enclosure 20 contains an array of power-driven rollers 27 for supporting each tire on its way into and out of the machine. As will be described below, spaces are required for operation of some of the tire handling mechanism, and permanently mounted power-driven rollers 27 are omitted in those spaces, but where intervening supports are required temporary rollers 28 on swing arms are placed in these spaces.

Just past the center of the enclosure, a sensing device is located which may be an electric eye but in this instance is shown as a mechanically operated electric switch 30 which shuts off the power to the rollers 27 and simultaneously starts the advance of a pair of tire supporting spools 31, transversely of the conveyor, in a suitable gap between the conveyor rollers. These spools 31 are mounted with vertical axes on a power-driven horizontally sliding frame, and are provided with lower flanges 35 and upper flanges 36, with the lower flanges just below the level of the conveyor rollers 27 and the upper flanges sufficiently higher to clear the largest tire which the machine is designed to handle.

A vertically directed electric eye 33, arranged to sense the absence of an obstruction, is placed equidistant from the two spools 31, that is, opposite to the switch 30 but about three-fourths of the distance across the conveyor from it. As the spools 31 are advanced in unison, they push the tire which closed the switch 30 directly across the conveyor until the electric eye 33 senses the absence of the tire by passage of the light beam through the bead circle. The signal from the electric eye directs a change of the advance of spools 31 from fast to slow motion. A second electric eye 34, a short distance beyond electric eye 33, similarly senses the passage of the tire and stops further advance of spools 31, with the tire positioned with one part of the circumference of its beads in a predetermined location such that the largest tire which the machine can handle will clear all structures on the side of the conveyor opposite from the side along which it entered the machine.

The second electric eye 34, in addition to stopping further advance of spools 31, starts the advance of another identical set of spools 32 which also have lower flanges 35 and upper flanges 36. In order to clear the light box of the preferred imaging system, which will be described below, the spools 32 are preferably advanced at an angle to the crosswise direction of the conveyor, and it is convenient to arrange them on swinging arms which are interconnected so as to move in unison through identical angles. When the spools 32 make contact with the tread of the tire in the machine, they compress the tire against spools 31, moving the tire bead back into the path of electric eye 34. This shuts off further advance of spools 32, and causes brief reversal of the drive to relieve the compression of the tire.

All four spools 31 and 32 are left in light contact with the tread surface of the tire in the machine, with sufficient pressure for rotating the tire, as will be described below, but not sufficient pressure to deform the tire significantly.

Figure 20:
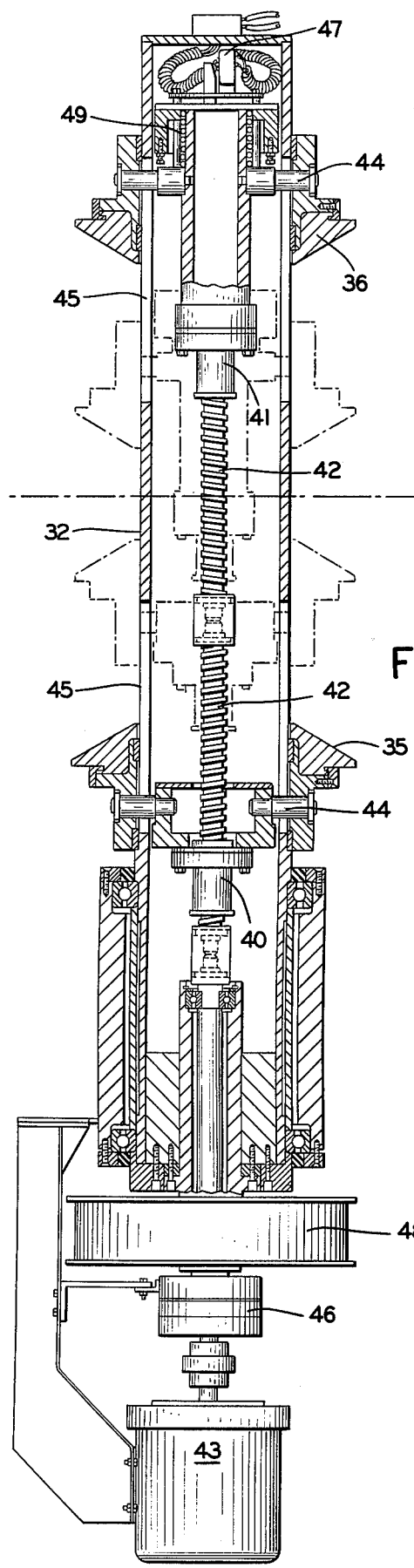
FIG. 20 is a vertical section through a tire supporting spool.

The second interruption of the beam of electric eye 34 not only stops horizontal motion of spools 32 but also triggers the mechanism for moving lower flanges 35 and upper flanges 36 of both sets of spools 31 and 32 vertically toward one another at equal speeds. This mechanism, shown in FIG. 20, includes inside the cylindrical part of each spool 31 and 32 a nut 40 with right hand thread and a nut 41 with left hand thread mounted on a right and left hand screw 42 driven by a motor 43. The nut 40 is connected to lower flange 35 and the nut 41 to upper flange 36 by means of a pin 44 in a slot 45 in the cylindrical body of each spool so as to prevent relative rotation between the nuts and the spools. Between the motor 43 and screw 42 is a magnetic clutch 46 which establishes a driving connection during operation of the motor 43 but releases the connection when motor 43 is not operating so as to permit freedom of rotation of the spool as a whole.

The connection between lower flange 35 and nut 40 is a solid connection so as to provide firm and immovable support, but the connection between upper flange 36 and nut 41 provides slight freedom of motion in the vertical direction against spring 49, with a micro switch 47 to sense the relative vertical motion.

The operation of the spool mechanism thus far described is that the second electric eye 34 activates motor 43 and magnetic clutch 46 of all spools 31 and 32, driving screw 42 to raise in unison all four of the lower flanges 35 and thereby lift the tire engaged by the four spools 31 and 32 while at the same time lowering all four upper flanges 36 until the upper flanges 36 rest upon the upper shoulder of the tire tread with sufficient force to lift the upper flanges 36 from their supports and activate switch 47, in each spool, which disengages both motor 43 and magnetic clutch 46. In addition, the number of revolutions of motor 43 is counted by a suitable built-in mechanism for controlling the extent of separation of the beads, as will be explained below.

The construction of spools 31 and 32 as just described is such tht lower flanges 35 and upper flanges 36 are always equidistant from a datum plane. The consequence is that a tire firmly gripped with one shoulder resting on lower flanges 35 and the other tread shoulder supporting upper flanges 36 will always have its midplane coincident with the datum plane, regardless of its size (unless it is an unsymmetrically designed tire, which is not ordinarily the case).

The precise placement of all tires, regardless of size or type, with their midplanes at a definite level, and with one side of the bead opening at a definite position both in the direction of entrance and exit of the tire, and also in the transverse direction, is an important feature of this invention. This precise placement greatly simplifies and facilitates automation of the tire handling procedure and also the production of the most useful kind of visual images as well as automated sensing of the presence of defects, as will be explained below.

In addition to the foregoing mechanism, each of the spools 31 and 32 is provided with a positive drive mechanism which is preferably a stepping motor (not shown) driving a cog belt pulley 48. The motor is arranged for rotating the tire in the machine through a succession of steps, each step being somewhat less then the distance required to advance the tire undergoing examination to present successive sectors of the tire for examination without overlap.

Since the tires which the machine is capable of examining vary in diameter over a wide range, from less than 20 inches (50 cm.) to 54 inches (137 cm.), the external circumferential distance through which the tire should be advanced in moving one sector after another into examining position also varies. Actually this distance, or sector width, is approximately proportional to section height, which can be sensed in various ways, such as by attaching a pulse generator to the driving mechanism for swinging spools 32 into position, and providing a means for counting the pulses and converting the count, at the moment of cessation of swinging motion of spools 32, into a command for the magnitude of each step of the stepping motors coupled to the driving pulleys 48. Thus, all four spools 31 and 32 are intermittently rotated in unison for stepwise advance of the tire without gaps and without excessive overlaps between tire sectors.

After the tire is properly positioned with its midplane in the predetermined datum plane, which is exactly midway between lower flanges 35 and upper flanges 36, the bead spreaders and X-ray tube are introduced into the center of the tire.

The bead spreaders in the embodiment shown are supported on a cage consisting of an upper cross member 50 and a lower cross member 51 solidly connected to essentially vertical guide rods 52. The upper cross member 50 has a pair of trunnions 53 which pivot through a small angle in fixed bushings, not shown, in a stationary part of the frame.

Figure 3:
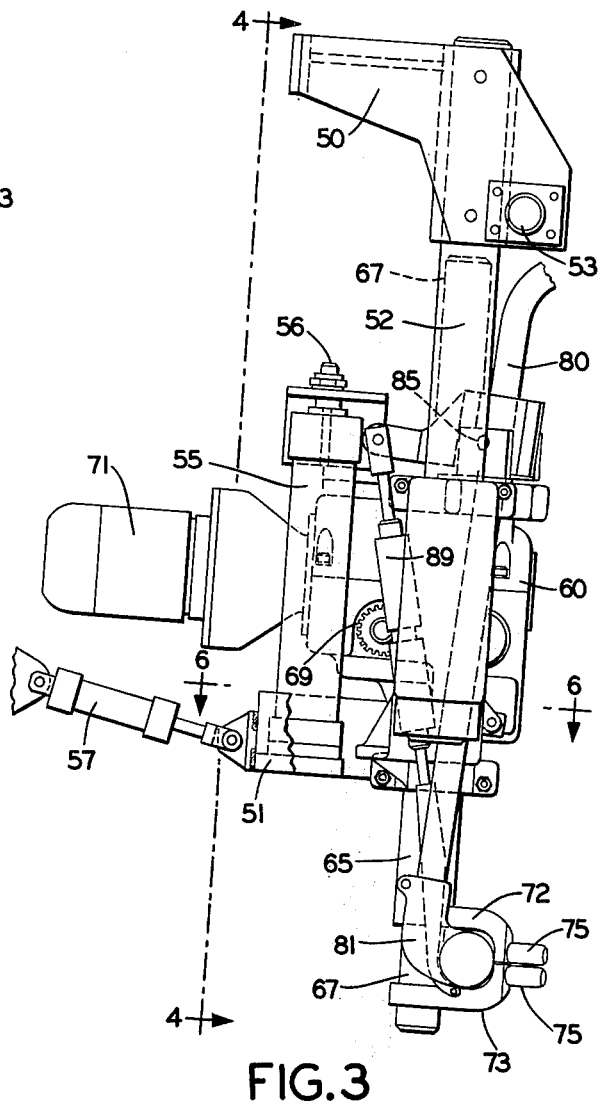
FIG. 3 is a view on a larger scale of the supporting mechanism for the X-ray tube and bead spreaders, looking toward the entrance end of the machine.
Figure 16:
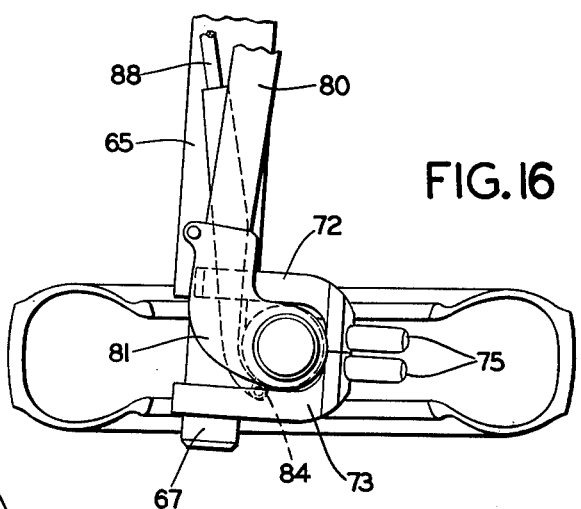
FIG. 16 is a partial section in a vertical plane, corresponding to FIG. 15.

The lower cross member 51 is offset in its center to clear the supported mechanism and to provide a base for cylinder 55, which has a piston rod 56 connected to a gear box 60 sliding vertically on guide rods 52. The lower cross member 51 is also connected to a short stroke horizontal cylinder 57, the opposite end of which engages a stationary frame member, for the swinging motion of the entire assembly in trunnions 53, from a retracted position as shown in FIG. 3 and FIG. 16, to a truly vertical operating position as shown in FIGS. 7 to 12, 17 and 19.

The gear box 60, as shown in FIGS. 12, 13, and 14, has aligned vertical cylindrical bores through which protrude, above and below, the ends of the bead spreader post consisting of a telescoping outer tube 65 having a rack 66 along part of its length, and a snugly fitting inner rod 67 having a rack 68 along part of its length. The tube 65 is slotted to expose rack 68. The racks 66 and 68 face in opposite directions and mesh with identical pinions 69 driven by a pair of identical worm gear drives having their worms 70 on a common shaft for actuation by a speed reducer and motor assembly 71. This motor, therefore, moves outer tube 65 and inner rod 67 at equal speeds and for equal distances in opposite directions.

To the bottom of outer tube 65 is welded an upper bent plate 72 extending horizontally and then vertically down. To the bottom of inner rod 67 is welded a lower bent plate 73 extending horizontally and then vertically upward to make contact with plate 72 in the closed position. On each bent plate 72 and 73 are a pair of horizontal stub axles a few inches (or centimeters) apart, on each of which is a freely rotatable bead spreader finger 75 about one inch (25 mm) in diameter and twice that long, with rounded ends. These fingers are placed so as to be in vertical contact when the spreader is closed, the fingers of each pair horizontally separated enough to be outside of the X-ray beam, and directed approximately radially of the tires when in operating position.

When motor 71 is activated in one direction, it will separate the bent plates 72 and 73 and the pairs of bead spreader fingers 75 mounted on them, and in the other direction it will move them together again.

Mounted on gear box 60 is a rigid conduit 80, which also functions as a support for the X-ray tube housing 81, and carries within it the wires and cables for heating the cathode and for the high voltage activating current, as well as the tubes for coolant supply. The X-ray tube 82 is of the type having the focal spot 83 from which the X-rays originate near one end, and is mounted for rotation on its longitudinal axis so that the X-rays can be pointed in various directions. The housing 81 has the end opposite the focal spot 83 offset for connection with the supporting conduit 80 to permit part of the housing to be between the beads of the being examined, even though the focal spot 83 from which the X-ray beam radiates is not between the beads or inside the tire.

Figure 5:
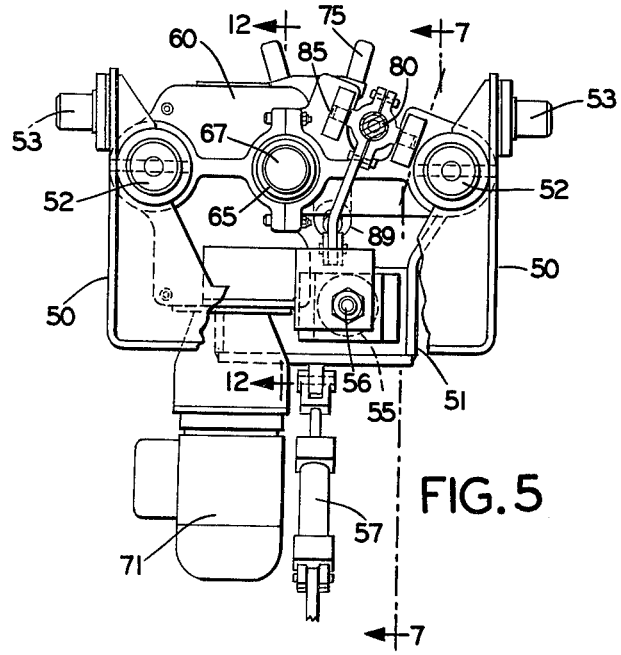
FIG. 5 is a plan view from the plane 5—5 of FIG. 4.
Figure 6:
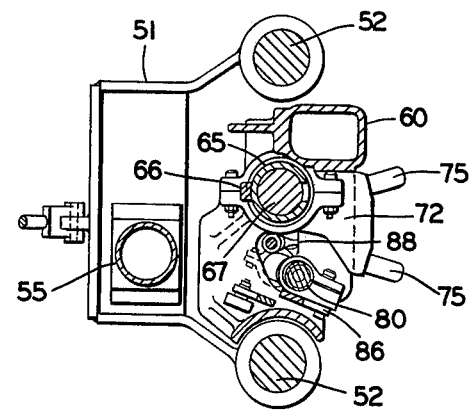
FIG. 6 is a sectional view through the plane 6—6 of FIG. 3.

The support and conduit 80 for the X-ray tube is mounted on gear box 60 by a pivot 85 shown in FIG. 5. This pivot 85 is not parallel to the trunnions 53 but at a slight angle so that the X-ray tube housing 81 can fit approximately centered in the bead circle of a tire, with its focal spot off center, and then swing in such a direction as to bring the focal spot 83 into a centered operating position, with the housing then off center. The actual swinging motion of the X-ray equipment is brought about by a toggle linkage 86 actuated by a cylinder 87, shown in FIG. 7 in an operating position and in FIG. 8 in a retracted position.

Figure 15:
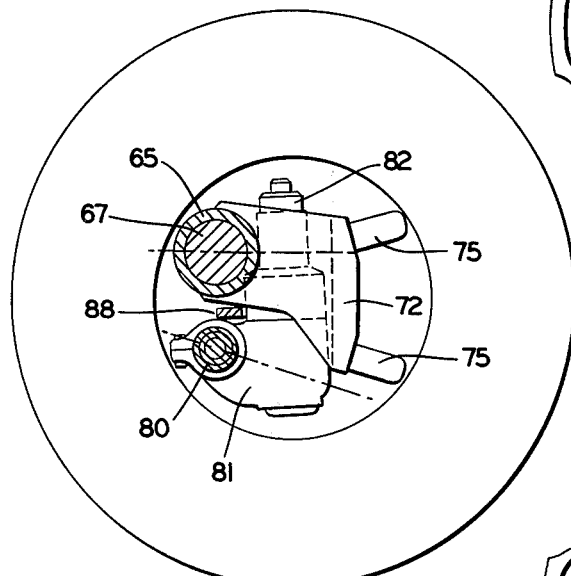
FIG. 15 is a plan view showing how the bead spreaders and X-ray tube fit in the smallest highway tire.

The functioning of the sub-assembly of bead spreader and X-ray tube is as follows. The tire which is to be examined is in its predetermined location with its midplane in the predetermined horizontal datum plane and with one part of the bead circle just above electric eye 34. The cylinder 55 lowers the gear box 60 to the extremity of its motion, positioning the closed bead spreaders and X-ray tube within the bead circle, and with the division between upper and lower bead spreader fingers 75, and also the focal spot 83, slightly above the datum plane. In the very smallest tire which the machine will accommodate, these parts fit with close but adequate clearance inside the bead circle as shown from above in FIG. 15 and in vertical section in FIG. 16.

This is a very desirable arrangement because it is not only extremely compact and mechanically simple, but also protects the somewhat fragile X-ray tube by surrounding it with strong structural members.

Figure 17:
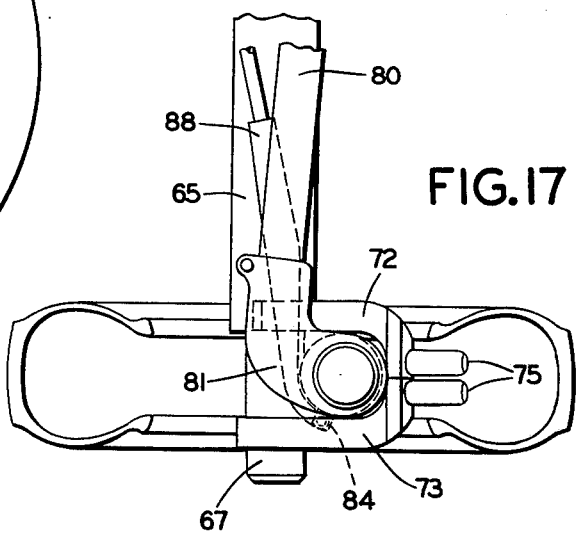
FIG. 17 is like FIG. 16 with the bead spreaders moved between the beads.

The cylinder 57 is then actuated to swing the assembly toward the imaging system and thrust the bead spreader fingers 75 between the tire beads, as shown in FIG. 17, with the X-ray tube still protected.

Motor 71 then moves tube 65 up and rod 67 down to an extent programmed from the previous sensing of section width, so that the bead spreader fingers separate the beads in the circumferential location closest to the imaging system, to a width approximating or slightly exceeding the maximum section width. This leaves a space between upper bent plate 72 and lower bent plate 73 into which the X-ray tube can move.

Figure 18:
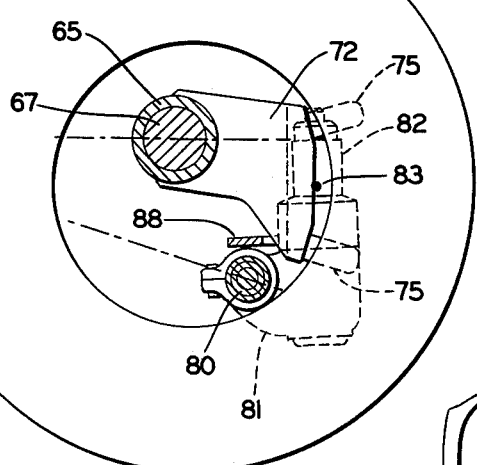
FIG. 18 is a plan view like FIG. 15 but with the bead spreaders and X-ray tube in operating position.
Figure 19:
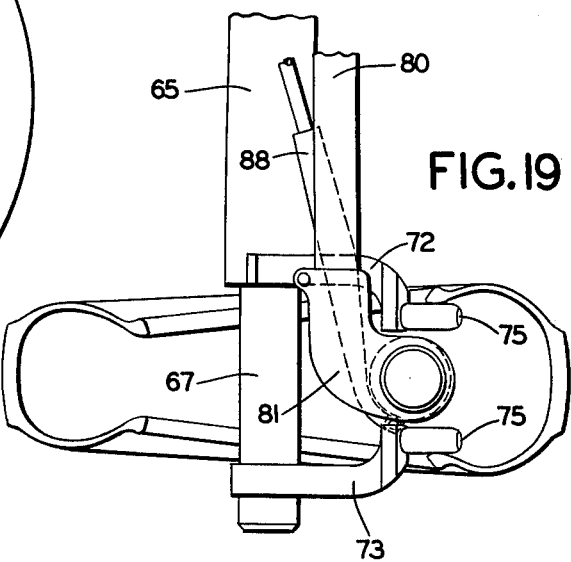
FIG. 19 is like FIGS. 16 and 17 but with bead spreaders and X-ray tube in the operating position shown in FIG. 18.

Cylinder 87 swings the X-ray tube 82 in its housing in a slightly diagonal path, positioning the focal spot in a centered position with respect to the image axis and also with respect to the four bead spreader fingers 75. In this final operating position shown in FIGS. 18 and 19 the telescoping tube 65 and rod 67, and also the X-ray tube support and conduit 80, are in essentially vertical positions, which is desirable for avoidance of any unbalanced stresses on the tire which might distort it and lead to spurious evaluations.

The particular spot chosen for location of the source of the X-rays—the focal spot 83—is the most advantageous from many points of view. It is symmetrical so that both sides of the tire can be examined with equal facility. It does not require distortions of the tire which could damage it in any way. It is enough away from all parts of each tire sector so that a reasonably area can be inspected without repositioning of either the tire or the X-ray source. At the same time, it is close enough for X-ray images of reasonable intensity, and also for examination of every part of the tire with X-rays passing through the tire at nearly a right angle to the surface. A rapid, meaningful, and accurate evaluation is the result.

During the X-ray inspection of the tire, X-ray tube 82 is rotated on its longitudinal axis to turn its focal spot 83 in several directions, preferably in three directions so as to direct the X-ray beam toward three adjacent fluorescent screens, a central vertical screen 90, an upper screen 91 tilted toward the X-ray source to receive an X-ray beam about 60° above the horizontal, and a lower screen 92 similarly tilted to receive an X-ray beam below horizontal. For this purpose the tube housing 81 is of the kind having bearings for the rotation of the tube, and flexible or sliding connections for the electric and coolant supply. A lug 84 on the X-ray tube is pinned to the lower end of connecting rod 88, the other end of which is joined to a pivot point on gear box 60 by axially aligned twin cylinders 89. The rod 88 is curved so as to fit around the curve of tube housing 81 when the rod 88 is in its most extended position.

The turning of the X-ray tube is in precise angles determined by the stroke of the pistons in the twin cylinders 89. As shown in FIG. 9, when both cylinders have their piston rods extended, the X-ray beam will be turned upward, toward upper fluorescent screen 91. When either one of the piston rods is retracted, the X-ray beam in its mid position will be turned toward central screen 90, as shown in FIG. 10. When both are retracted, the X-ray beam will be turned downward as shown in FIG. 11, toward lower screen 92.

The screens 90, 91, and 92, or their equivalents, are the input end of the imaging system. For visual inspection, the imaging system is preferably constructed for display of a composite image of the entire internal structure of a tire sector from bead to bead as described and claimed in the application for patent identified in the introductory paragraph. For automated inspection, various kinds of devices for sensing and comparing intensity of transmitted radiation may be used with or instead of the visual means.

The visual imaging equipment in its presently preferred form has the three fluorescent screens 90, 91, and 92 closely adjoining, so that they will present shadow pictures of an entire tire sector, with upper screen 91 showing one bead and sidewall, central screen 90 showing the shoulders and tread portion, and lower screen 92 showing the other sidewall and bead. These screens are enclosed in a light box 95 with light-absorbent black interior surfaces.

Facing central screen 90 at a 45° angle, inside light box 95, as indicated by dash lines in FIG. 1, is a mirror 96 to reflect the image on the screen at a right angle horizontally. Other mirrors 97 and 98 reflect the image again at right angles and a rotating mirror 99 reflects the image into the lens of a video camera 100. The purpose of the succession of mirrors is simply to bring the camera 100 close enough so that it can view all three screens 90, 91, and 92 with the same focus and the same magnification.

Facing upper screen 91 at an angle of approximately 45°, inside light box 95, as shown by dash lines in FIG. 2, is a mirror 101. The light from it is reflected again, at an obtuse angle, by mirror 102 at about 30° to the vertical. The exact position and angle of these mirrors is such that the light path screen 90 and its image is transferred to another third of the target of the storage tube, followed in the same manner by the image of the other side of the tire on the last third of the target of the storage tube. The composite image of the tire sector so formed is then read out of the storage tube for continuous display as a still picture on the picture tube of a television monitor.

While the composite image is being displayed on the monitor, the tire supporting spools 31 and 32 are rotated through the angle programmed from the sensing of section height, so as to bring another sector of the tire into the field of view. The transfer of the shadow pictures on the three screens to different thirds of the target of a second storage tube then occurs in the same manner, followed by display of that composite picture, replacing the previous one on the monitor, and then storage of the next composite picture in the first storage tube, and so on alternately.

Only a second or two are required for production and display of each composite image, and are also sufficient for determination of the presence of an irregularity constituting an objectionable defect in the tire sector under observation, when it is presented as a still picture. With screens of a suitable size, the number of steps for complete inspection of an entire small tire can be considerably less than a minute and for the largest tire not much more, because the geometry of the system is such that the walls of large tires are farther from the X-ray source than small tires, so that the number of sectors from screen 91, when the rotating mirror 99 is in the proper position, is of exactly the same length as that from central screen 90 and enters the camera 100 along its axis. A similar series of mirrors reflects the image from lower screen 92 into the camera 100 when rotating mirror 99 faces in the proper direction.

The rotating mirror 99 may be faced toward each light path in turn by a Geneva drive, suitably coordinated with other steps of the machine operation, since such a drive will turn through an exact angle and then remain at rest for a period of time.

Since each mirror reverses the image, an odd number of reflections leave the image reversed, but an even number will rereverse and leave the image in its original posture. In this embodiment the four reflections of the image on central screen 90 present it to the camera in the proper posture, but the three reflections of upper and lower screens 91 and 92 present a reversed image. Accordingly the electric circuits connected to the camera 100 are so chosen as to scan the electronic images of screens 91 and 92 in the opposite direction from that of screen 90 to bring them all into the same relation to the viewer.

A composite image is formed by turning X-ray tube 82 toward one sidewall and bead to form a shadow picture on the corresponding screen, with rotating mirror 99 in the proper position, and then transferring the electronic image in the video camera 100 to one-third of the width of the target of a storage tube. The X-ray tube and mirror are then turned toward the central screen 90 and its image is transferred to another third of the target of the storage tube, followed in the same manner by the image of the other side of the tire on the last third of the target of the storage tube. The composite image of the tire sector so formed is then read out of the storage tube for continuous display as a still picture on the picture tube of a television monitor.

While the composite image is being displayed on the monitor, the tire supporting spools 31 and 32 are rotated through the angle programmed from the sensing of section height, so as to bring another sector of the tire into the field of view. The transfer of the shadow pictures on the three screens to different thirds of the target of a second storage tube then occurs in the same manner, followed by display of that composite picture, replacing the previous one on the monitor, and then storage of the next composite picture in the first storage tube, and so on alternately.

Only a second or two are required for production and display of each composite image, and are also sufficient for determination of the presence of an irregularity constituting an objectionable defect in the tire sector under observation, when it is presented as a still picture. With screens of a suitable size, the number of steps for complete inspection of an entire small tire can be considerably less than a minute and for the largest tire not much more, because the geometry of the system is such that the walls of large tires are farther from the X-ray source then small tires, so that the number of sectors required for complete circumferential inspection will not differ greatly from one size to another.

If a defect is observed by the operator, he can actuate a marking device which will project a spot of color on or near the defective area, and also actuate a diversion gate for segregation of the defective tire for special handling. Moreover, a temporary or permanent record of the nature of the defect can be prepared easily by photographing the picture displayed on the monitor, or by transferring the image in the storage tube to magnetic film or disc for more leisurely examination in a different location.

When the machine has presented the entire circumference of a tire for inspection, by operating the required number of cycles or steps for a particular size of tire, the programming equipment will retract the X-ray tube into the bead circle, bring the bead spreader fingers together and retract them into the bead circle, lift the assembly out of the tire, separate the flanges of the spools to lower the tire, and restart the conveyor rollers to carry the tire out of the machine.

If it is desired to use the machine for determining only the regularity of location of such structures as the circumferential belt under the tread, or the bead and associated elements such as flippers, the tire can be rotated continuously instead of stepwise, and the image on each screen can be transferred to a part of a picture tube or to an entire tube.

If it is found to be inconvenient to obtain partial images which exactly match at their edges, because of physical problems of bringing edges of the several fluorescent screens exactly together, or of reproducing the images with their edges exactly coinciding or if it is desired to produce partial images which will have slightly overlapping edges for some other reason, it may be preferred to have the X-ray source for the several partial images slightly displaced from a common point of origin, in a direction away from the screens. For this purpose, it is only necessary to mount the X-ray tube in its rotating support slightly off center so that the focal spot will be slightly farther from the fluorescent screen in each position than the axis of rotation of the X-ray tube.

If it is desired to automate the actual inspection in whole or in part, instead of relying entirely on visual inspection by a human operator, it is helpful to regulate the intensity of the radiation to a constant level, to establish a norm from which deviations can be measured. This is also useful for other reasons, such as for extending the life of the X-ray tube by reducing the voltage during inactive intervals and stepping it up again to a level which will produce a predetermined intensity after passing through the tire wall.

Accordingly, it is preferred to mount radiation sensing devices for use in controlling the intensity of radiation. In the ususal case in which fluorescent screens are used, it is simplest to sense the visible light produced by the screens. This is easily accomplished by suitable placement of one or two photocells of the kind which focus light from a spot onto the photosensitive element. In the case of the imaging system specifically described above, with mirrors to reflect the shadow pictures on fluorescent screens into a single video camera, one or two photocells 105 may be mounted on or near the edges of the first mirror 96 for the central screen, and another one or two photocells 106 on or near the edges of the first mirror 101 for the upper screen and the corresponding mirror for the lower screen, as shown in FIGS. 21 and 22.

These photocells are then connected to the programming equipment in such a way that when a tire is in position for examination with its beads spread and the X-ray tube is being thrust into its operating position the voltage is raised until the brightness of the image on the fluorescent screen 90 or 91 (or 92), as the case may be, reaches an optimum level for which the electric circuits have been adjusted. The voltage is then automatically maintained at the same level until the X-ray beam is shifted to another screen, and the voltage is automatically returned to the same level again when the X-ray beam is shifted back to the same screen for examination of another sector of a tire. If, as is frequently the case, densities of different portions of tires are markedly different, as when steel cords are in the belts under the treads but are absent from the sidewalls, the electrical equipment may be programmed to direct high voltage X-ray to the dense areas and lower voltage X-rays to the others, in response to the different sensings of the photocells.

The same kind, or different kins, of photocells can be used not only for automatic regulation of the X-ray source as mentioned above, but also for actual automated sensing of irregularities in structure, such as constitute defects which may cause concentrations of stress and lead to premature failure. For this purpose, one or a few photocells may be programmed to signal variations in circumferential density such as result from crowding of cords or abnormally wide spacing of cords. Such signals can be arranged to activate a reject gate so that the particular tire can be excluded from sale or use, or can be subjected to more careful scrutiny to determine whether it is acceptable for use.

As indicated above, automated inspection can occur simultaneously with visual inspection, in which case it is preferred to carry out the visual part of the inspection stepwise with visual examination of a succession of still pictures. However, it is equally possible to employ either or both modes of inspection with the tire in continuous uniform rotation.

If only automated inspection is being employed, it can be preferred to rotate the tire continuously at a uniform speed for slightly more than one revolution. Because of the speed of response of suitable photocells, such inspection can be much more rapid than visual inspection, twice or more times as fast.

For automated inspection of random sizes and types of tires, it may be sufficient to provide as the sole radiation responsive devices a sequence of radiation sensitive elements 108 across all or any desired part of the beam or beams of X-rays or other penetrating radiation. Such elements 108 can either be directly responsive to X-rays or can contain a fluorescent material combined with a photoelectric element. The elements 108 are then connected individually or collectively to control circuits such that uniform intensity throughout the revolution of a tire will produce no response, but either local or extensive variation of intensity will produce a signal which can be used to reject the tire or to divert it for special handling.

As an example of local variation, a foreign object can cause a shadow to pass across the field. As another example, a partial lateral displacement of a belt ply can cause a particular photoelement to be brightly illuminated in one part of the circumference and dimly illuminated in another part of the circumference. In both instances the tire is clearly imperfect.

As an example of a more extensive departure from normal, a tread ply or plies may be laterally displaced as a whole, so that the margin of the belt, although a true circle, is farther from the midplane on one side than on the other. Such a situation can also be detected automatically by programming the equipment to sense a different number of intensely radiated elements on one side than on the other, or a different length of a radiation sensitive strip, and in such event to reject the tire.

With different designs of tires, different factors will be important and can be detected easily with machines made in accordance with this invention, because of the precision of placement of the tires with their midplanes exactly in a predetermined datum plane and their beads placed in an exact location relative to the radiation sensing equipment. This precision of placement gives the visual observer a clear guide as to symmetry and uniformity and gives an automated system a precise datum plane from which symmetry and dimensional differences can be sensed automatically.

We claim:
1. In a tire inspection machine
   means for sensing the presence of one side of the
   a. bead opening of a pneumatic tire in a predetermined position;
   b. means for moving the one side of the bead opening toward the predetermined position;
   c. means, responsive to the means for sensing, for terminating the motion of the side of the bead opening;
   d. means for engaging one shoulder of the tread of the tire and opposing means for engaging the other shoulder, which means are positively driven toward one another at identical speeds axially of the tire for positioning the tire with its midplane coinciding with a predetermined plane;
   e. means having a predetermined location with respect to the predetermined position and predetermined plane, for indicating the presence of structural irregularities in a tire and the location of the irregularities with respect to the predetermined plane.
2. A machine as in claim 1, in which the means for sensing the presence of one side of the bead opening of a pneumatic tire includes a narrow radiant beam and a transducer.
3. A machine as in claim 1, in which the means for indicating the presence of structural irregularities includes a source of X-rays within the bead circle of the tire.
4. A machine as in claim 3, in which means are provided for forcefully separating at least the portions of the beads nearest to the predetermined position.
5. A machine as in claim 4, in which the source of X-rays is close to the predetermined position and predetermined plane.
6. A machine as in claim 5, in which fluorescent screens are located on the outside of the tire opposite to the source of X-rays for receiving a shadow picture of an entire sector of a tire from bead to bead.
7. A machine as in claim 5, in which the source of X-rays and the means for separating the beads are on a common support and are movable together into the bead circle.
8. A machine as in claim 7, in which the means for separating the beads are movable from a closed position surrounding the source of X-rays to an open position in which the tire beads are spread and in which there is clearance for advancement of the source of X-rays radially outward.
9. A machine as in claim 1, in which the tire inspection machanism includes a source of penetrating radiation on the radially inward side of the tire wall and means on the radially outward side of the tire wall for sensing irregularities in the intensity of transmitted radiation in a particular location transversely of the tire.
10. A machine as in claim 9, in which the means for sensing irregularities are closely adjacent plural means which will collectively indicate the location of the edge of a circumferential tire element.
11. A machine as in claim 9, in which the means for sensing irregularities are plural means spaced across the width of the beam of radiation.
12. In a tire inspecting machine, means for rotably supporting a tire in a fixed position, a source of X-rays, a means for separating the beads of the tire, and a common support for the source of X-rays and the means for separating the beads, the common support being movable to position both the source of X-rays and the means for separating the beads alternately in a position within the bead circle of a tire supported in the fixed position and in a position completely outside of the bead circle of the tire.
13. A machine as in claim 12, in which the means for separating the beads are movable from a closed position surrounding the source of X-rays to an open position in which the tire beads are spread and in which there is clearance for advancement of the source of X-rays radially outward.
14. A machine as in claim 12, in which the source of X-rays and means for separating the beads of the tire are jointly movable radially between the position within the bead circle of the tire and a position in which the means for separating the beads are between the beads of the tire.
15. A machine as in claim 14, in which the means for separating the beads are movable from a closed position surrounding the source of X-rays to an open position in which the tire beads are spread and in which there is clearance for advancement of the source of X-rays radially outward.
16. A machine as in claim 15, including means for moving the source of X-rays radially outward toward the bead circles of the tire.

* * * * *

UNITED STATES PATENT OFFICE
CERTIFICATE OF CORRECTION

Patent No. 3,934,144  Dated January 20, 1976

Inventor(s) Donald T. Green, et al

It is certified that error appears in the above-identified patent and that said Letters Patent are hereby corrected as shown below:

Column 6 line 22, correct the spelling of "that"

Column 6 line 46(47), change "then" to ---than---

Column 7 last line, before "being" insert ---tire---

Column 8 line 7 from bottom, after "It is" insert ---far---

Column 8 line 6 from bottom, after "reasonably" insert ---large---

Column 9 line 64 commencing with "screen 90" cancel the passage ending at Column 10 line 26 with "sectors", which is a duplication of the passage commencing at Column 10 line 56.

Column 12 line 5, correct the spelling of "usual"

Column 12 line 39, correct the spelling of "kinds"

Claim 1 line 2 at the beginning of the line insert ---a.---

Claim 1 line 3 cancel "a."

Claim 1 line 8, before "side" insert ---one---

Signed and Sealed this thirtieth Day of March 1976

[SEAL]

Attest:

RUTH C. MASON
Attesting Officer

C. MARSHALL DANN
Commissioner of Patents and Trademarks